United States Patent
Willuweit

(10) Patent No.: US 9,210,937 B2
(45) Date of Patent: Dec. 15, 2015

(54) COMPOSITION FOR DESTROYING THREAD ALGAE

(71) Applicant: Söll GmbH, Hof (DE)

(72) Inventor: Thomas Willuweit, Hof (DE)

(73) Assignee: Söll GmbH, Hof (DE)

( * ) Notice: Subject to any disclaimer, the term of this patent is extended or adjusted under 35 U.S.C. 154(b) by 0 days.

(21) Appl. No.: 14/182,680

(22) Filed: Feb. 18, 2014

(65) Prior Publication Data

US 2014/0171324 A1    Jun. 19, 2014

Related U.S. Application Data

(63) Continuation of application No. 12/089,207, filed as application No. PCT/DE2006/001758 on Oct. 6, 2006, now abandoned.

(30) Foreign Application Priority Data

Oct. 7, 2005 (DE) .......................... 10 2005 048 460

(51) Int. Cl.
| | |
|---|---|
| *A01N 59/00* | (2006.01) |
| *A01N 59/04* | (2006.01) |
| *C01B 15/10* | (2006.01) |
| *C02F 1/50* | (2006.01) |
| *C02F 1/66* | (2006.01) |
| *C02F 1/72* | (2006.01) |
| *C02F 103/20* | (2006.01) |

(52) U.S. Cl.
CPC ................ *A01N 59/00* (2013.01); *A01N 59/04* (2013.01); *C01B 15/103* (2013.01); *C02F 1/50* (2013.01); *C02F 1/66* (2013.01); *C02F 1/722* (2013.01); *C02F 2103/20* (2013.01)

(58) Field of Classification Search
None
See application file for complete search history.

(56) References Cited

U.S. PATENT DOCUMENTS

| | | | |
|---|---|---|---|
| 4,926,795 | A | 5/1990 | Hamilton et al. |
| 5,207,925 | A | 5/1993 | Steiner et al. |
| 5,855,874 | A | 1/1999 | Gopalkrishnan et al. |
| 6,054,066 | A | 4/2000 | Honig et al. |
| 6,569,342 | B1 | 5/2003 | Willuweit et al. |
| 2004/0101944 | A1 | 5/2004 | Willuweit et al. |
| 2004/0219190 | A1 | 11/2004 | Kosti |
| 2005/0155937 | A1 | 7/2005 | Zawada et al. |
| 2007/0021315 | A1 | 1/2007 | Weber |
| 2008/0262098 | A1 | 10/2008 | Willuweit |

FOREIGN PATENT DOCUMENTS

| | | |
|---|---|---|
| DE | 10 2004 003286 | 9/2005 |
| EP | 0 427 314 A2 | 5/1991 |
| EP | A-623553 | 11/1994 |
| EP | 0 968 136 | 9/1998 |
| EP | 0 884 276 A1 | 12/1998 |
| EP | A-1227063 | 7/2002 |
| EP | 1 557 088 | 7/2005 |
| GB | 2375543 | 11/2002 |
| JP | 2296705 A | 7/1990 |
| NL | 1017129 | 7/2002 |
| WO | WO 98/17592 | 4/1998 |
| WO | WO 99/58457 | 11/1999 |
| WO | WO 2007/041992 | 4/2007 |

OTHER PUBLICATIONS

International Preliminary Report on Patentability corresponding to International Application No. PCT/DE2006/001758 dated Jun. 11, 2008.
International Search Report corresponding to International Application No. PCT/DE2006/001758 dated Sep. 12, 2007.
Office Action corresponding to U.S. Appl. No. 12/089,207 dated Aug. 15, 2013.
Office Action corresponding to U.S. Appl. No. 12/089,207 dated Feb. 1, 2012.
Office Action corresponding to U.S. Appl. No. 12/089,207 dated Jun. 16, 2010.
Office Action corresponding to U.S. Appl. No. 12/089,207 dated Nov. 24, 2010.
Office Action corresponding to U.S. Appl. No. 12/089,207 dated Oct. 26, 2011.
Written Opinion of the International Searching Authority corresponding to International Application No. PCT/DE2006/001758 dated Jun. 5, 2008.

*Primary Examiner* — Jeffrey S Lundgren
*Assistant Examiner* — William Lee
(74) *Attorney, Agent, or Firm* — Jenkins, Wilson, Taylor & Hunt, P.A.

(57) ABSTRACT

A composition of alkali carbonate peroxyhydrate in a quantity of 45 to 85% by weight relative to a total amount of the composition and an alkali hydrogen carbonate is provided for combating pathogenic germs and parasites in water of aquaculture, ponds, and aquariums; for destroying thread algae in water; for processing water. The addition of alkali hydrogen carbonate to alkali percarbonate peroxyhydrate stabilizes the alkali percarbonate peroxyhydrates relative to combustible materials. The alkali carbonate peroxyhydrate is preferably $Na_2CO_3$ and $xH_2O_2$.

9 Claims, No Drawings

COMPOSITION FOR DESTROYING THREAD ALGAE

RELATED APPLICATIONS

The present application is a continuation of U.S. patent application Ser. No. 12/089,207, filed Apr. 4, 2008, which itself was a United States National Stage Application of PCT/DE2006/01758, filed Oct. 6, 2006, which itself claimed the benefit of German Patent Application Serial No. DE 10 2005 048 460.3, filed Oct. 7, 2005. The disclosure of each of these applications is incorporated herein by reference in its entirety.

BACKGROUND OF THE INVENTION

The present invention relates to a composition containing alkali carbonate peroxyhydrates and alkali hydrogen carbonates as well as the use of this composition for combating thread algae, germs and parasites in waters and sediments and on surfaces, and the use of alkali hydrogen carbonates for stabilizing alkali carbonate peroxyhydrates.

In aquariums as well as garden ponds thread algae are a type of algae that often turns into a plague. With regard to classification the thread algae belong to lower plants and are assigned to the class of green algae (Chlorophyta). A majority of known green algae species is indigenous to freshwater. Species of the genera *Ulothrix, Spirogyra* and *Cladophora* present regularly a great problem for many garden pond owners in the spring and summer when these algae species as a result of mass multiplication form a carpet of algae that can only be removed with difficulty from the water.

Thread algae colonize generally also directly on surfaces and walls as well as on loose sediment and rocks as well as on technical devices such as filters pumps, pipes, aeration devices etc. so that impairments are also caused thereon.

The causes for algae growth are often a surplus of nutrients and light. In the prior art it is known as a measure for combating this to add fast-growing plants to the aquarium or the garden pond in order to take away the nutrient source from the thread algae. However, until such a measure shows an effect, several weeks can pass and an algae-free aquarium or garden pond is not obtained. As a further fast reducing measure a change of the water is recommended. This measure is also in many cases not practicable. The same holds true for reducing the light; this is possible for aquariums but not for a garden pond.

An ecologically innocuous agent for destroying thread algae is sodium carbonate peroxyhydrate, also known as sodium percarbonate. Further fast acting and effective agents are chemical algicides that contain active ingredients such as terbutryn, monolinuron, zinc and copper salts. None of the known preparations has a selective effect on thread algae. By using such algicides, at the same time the water quality is worsened and the growth of plants reduced so that in some cases plants can be completely killed off.

A disadvantage of sodium carbonate peroxyhydrate is its minimal stability, its sensitivity relative to water and heat. Upon extended or improper storage, the substances can decompose so that they can no longer develop their actual action. Because of the minimal stability and the oxidizing effect the substance is subject to transport, storage, and commercial regulations.

As a whole, alkali carbonate peroxyhydrates are ecologically well tolerated substances that can be employed advantageously in water processing and also for combating pathogenic germs in aquaculture, in aquarium water and garden ponds etc. It is disadvantageous that, as a result of their hazard potential, they can be transported and stored only under strict safety regulations and that commercial trade is limited.

European patent application EP 0 968 136 discloses the use of alkali percarbonate peroxyhydrates in fish farming. This document discloses the use of these substances for oxygen-delivering, neutralizing, and degerming processing of waters in freshwater as well as saltwater installations, natural bodies of water etc. According to this document the alkali carbonate peroxyhydrates provide in particular a degerming action.

The present invention thus has the goal to provide a composition that enables safe transport and long-term storage without having the oxidizing risk potential of alkali carbonate peroxyhydrates.

SUMMARY OF THE INVENTION

Object of the present invention is thus a composition, containing alkali carbonate peroxyhydrates and alkali carbonates and/or hydrogen carbonates, that is characterized in that the alkali carbonate peroxyhydrate is contained in an amount of more than 0 up to 85% by weight relative to the total amount of the composition.

By addition of alkali carbonates and/or hydrogen carbonate it is possible to stabilize the alkali carbonate peroxyhydrates so that the substance can be transported well and can also be stored well. The addition of alkali carbonates and/or hydrogen carbonates has the advantage that this component does not impair the use of peroxyhydrates for processing water but instead even has a positive effect on the water. The carbonates or hydrogen carbonates act as stabilizers for the peroxo compounds and compensate thus their oxidizing effect.

As alkali carbonate peroxyhydrates, lithium, sodium, potassium and/or rubidium compounds can be used wherein sodium carbonate peroxyhydrate is preferred. When using the composition according to the invention as an additive in bodies of water such as aquariums and garden ponds, minimal quantities of the potassium compound may be contained; however, these quantities should be not be too high because large quantities of potassium can be poisonous to fish.

In the composition according to the invention the alkali carbonate peroxyhydrate can be contained in a quantity of up to 85% by weight. Preferred compositions contain these substances in a quantity of 45 to 85% by weight, in particular 74 to 82% by weight.

As a further substance the composition according to the invention contains alkali hydrogen carbonate wherein in regard to these compounds the sodium compounds are also preferably used. The hydrogen carbonates have the advantage that they exhibit a milder pH value than carbonates and mixed with the alkali carbonate peroxyhydrate provide directly a buffer system that has a positive effect on the water to be processed. Inasmuch as the composition according to the invention is used as an agent for processing water, further components can be also added that have a positive effect on the water quality. For example, components can be contained that have a microbiological effect. Examples for substances that can be added as supplements are earth alkali compounds such as calcium salts, chelating agents, alginates, microbiological cultures etc.

DESCRIPTION OF THE PREFERRED EMBODIMENTS

When destroying thread algae or when microbiologically decomposing the cell substance, nitrates and phosphates are released that can serve as nutrients for growth of new thread algae. In order to keep the quantity of nutrients being generated minimal, it has been found to be advantageous to add to the composition according to the invention earth alkali compounds, in particular earth alkali peroxides, preferably $CaO_2$. The additives can be contained in the composition according to the invention in quantities of up to 10% by weight, preferably up to 5% by weight and in particular up to 2.5% by weight.

As further components, the mixture according to the invention can contain microorganisms. The microorganisms can be selected from autotrophic and heterotrophic microorganisms, in particular chemolithoautotrophic nitrifying microorganisms such as ammonia oxidizing microorganisms and nitrite-oxidizing microorganisms, heterotrophic nitrifying microorganisms such as fungi of the genera *Aspergillus, Penicillium,* and *Cephalosporium,* algae, *Arthrobacter* sp., *Alcaligenes* sp., *Nocordia* sp., *Bacillus azotoformans, Sporosarcina psychrophila, Pseudomonas* and any mixture of the aforementioned heterotrophic denitrifying microorganisms such as *Paracocus* sp. and *Pseudomonas* sp. and any mixture of the above.

The microorganisms can be contained in a quantity of 0.5 to 4% by weight relative to the total composition.

The composition according to the invention is characterized in particular in that it inhibits growth of thread algae, i.e., destroys the thread algae. This means that the thread algae are lysed and die off. A further object of the present invention is accordingly the use of the composition according to the invention of alkali carbonate peroxyhydrate and alkali carbonate and/or hydrogen carbonate for destroying thread algae.

The addition of alkali hydrogen carbonates to alkali percarbonate peroxyhydrates can significantly improve the stability of these peroxo compounds. A further object of the present invention is therefore the use of alkali hydrogen carbonates for stabilizing alkali percarbonate peroxyhydrates. The two components are preferably present in a ratio of alkali hydrogen carbonate to alkali percarbonate peroxyhydrate in a ratio of 15:85 to 35:65. This quantitative ratio should be maintained also in mixtures with additional components.

A further object of the present invention concerns the use of the composition for combating pathogenic germs and parasites in aquaculture, artificially installed ponds, such as garden ponds, and natural ponds, lakes, and aquariums.

Another object of the present invention concerns the use of the composition for processing water, bodies of water, and sediments.

EXAMPLES

Test of the Oxidizing Effect of a Mixture of Alkali Carbonate Peroxyhydrate and $NaHCO_3$ The test procedures for determining the oxidizing effect of substances are provided in EU regulation 67/548, part 2. The oxidizing effect of substances may not surpass at most that of $Ba(NO_3)_2$: cellulose=7:3.

1. A mixture of sodium carbonate peroxyhydrate and $NaHCO_3$ with 80% by weight sodium carbonate peroxyhydrate and 20% $NaHCO_3$ on cellulose in a ratio of 7:3 was tested.

As sodium carbonate peroxyhydrate commercial-grade qualities were tested. The particle size of the components in the mixture was <125 µm.

Results

|   | Comparative sample | Sample according to the invention |
|---|---|---|
| A. | 2.6 mm/s +/+ 0.2 mm/s | 1.4 mm/s +/+ 0.1 mm/s |
| B. | 2.9 mm/s +/+ 0.2 mm/s | 1.0 mm/s +/+ 0.1 mm/s |

2. A mixture of sodium carbonate peroxyhydrate and $NaHCO_3$ in the composition as in Example 1 was tested with regard to different proportions of cellulose of 1:9 to 9:1.

The highest value of the measured oxidizing effect was 1.1 mm/s 0.1 mm/s.

The results show that already with a minimal addition of $NaHCO_3$ the oxidizing effect of sodium carbonate peroxyhydrate can be lowered such that it is no longer considered a hazardous material according to EU regulations.

Use in Water Treatment

In a pond on a golf course the existing thread algae mass multiplication was eliminated within 24 hrs. by adding a mixture of 80% sodium carbonate peroxyhydrate and 20% sodium bicarbonate. After removal of the died-off algae biomass, the body of water was free of thread algae.

What is claimed is:

1. A composition consisting essentially of: an alkali carbonate peroxyhydrate in a quantity of 74 to 82% by weight relative to a total amount of the composition; and an alkali hydrogen carbonate as a stabilizer for the alkali carbonate peroxyhydrate; wherein the composition has an oxidizing effect that does not surpass that of Ba(NO3-)2:cellulose 7:3 when tested as set forth in European Union (EU) Regulation 67/548, part 2, and further wherein the ratio of alkali hydrogen carbonate to alkali carbonate peroxyhydrate is from 15:85 to 55:45.

2. The composition according to claim 1, wherein the alkali carbonate peroxyhydrate is 2 $Na_2CO_3$ ·3 $H_2O_2$.

3. The composition according to claim 1, wherein the alkali carbonate peroxyhydrate is a mixture of $Na_2CO_3$ and $H_2O_2$.

4. The composition according to claim 1, wherein the alkali carbonate peroxyhydrate and the alkali hydrogen carbonate are present in a ratio of 85:15 to 65:35.

5. The composition according to claim 1, wherein the composition further comprises 1-10% by weight of an earth alkali peroxide.

6. The composition according to claim 1, wherein the composition contains 0.5% by weight to 4% by weight of microorganisms relative to the total amount of the composition.

7. A method of combating pathogenic germs and parasites in the water of aquaculture, ponds, and aquariums, the method comprising:
(a) providing a composition according to claim 1; and
(b) adding the composition according to claim 1 to the water.

8. A method for destroying thread algae in water, the method comprising:
(a) providing a composition according to claim 1; and
(b) adding the composition according to claim 1 to the water.

9. A method of producing a composition comprising stabilized alkali percarbonate peroxyhydrate relative to combustible materials, the method comprising adding alkali hydrogen carbonate to alkali percarbonate peroxyhydrate in a ratio of alkali hydrogen carbonate to alkali carbonate peroxyhydrate of from 15:85 to 55:45, wherein the alkali percarbonate peroxyhydrate is stabilized such that it has an oxidizing effect that does not surpass that of Ba(NO3)2:cellulose 7:3 when tested as set forth in European Union (EU) Regulation 67/548, part 2, wherein the alkali carbonate peroxyhydrate is present in a quantity of 74% by weight to 82% by weight relative to the total amount of the composition.

\* \* \* \* \*